Figure 1:
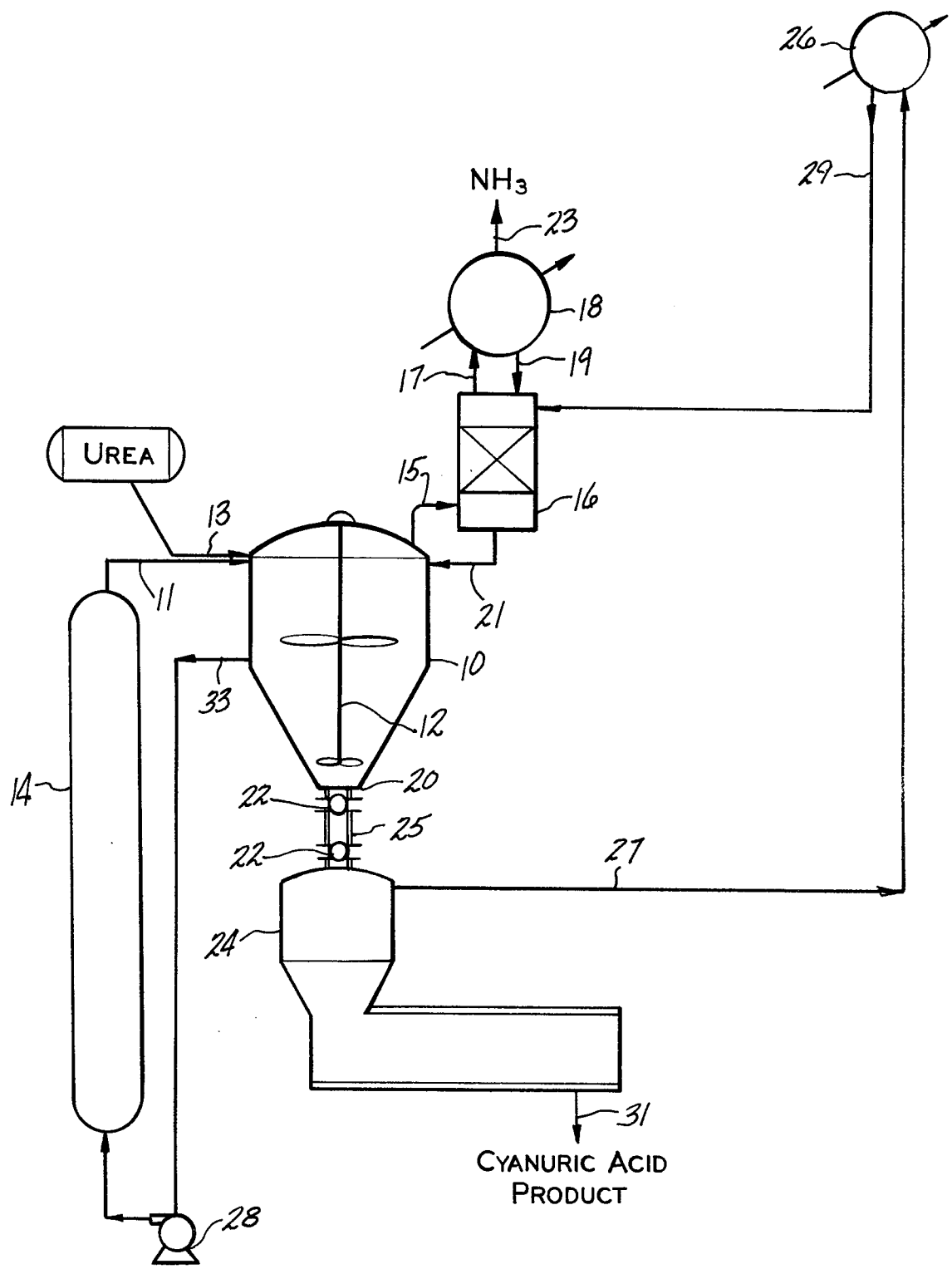

United States Patent [19]

Bartoszek et al.

[11] 4,237,285
[45] Dec. 2, 1980

[54] PROCESS FOR THE PRODUCTION OF CONCENTRATED CYANURIC ACID SLURRIES

[75] Inventors: John A. Bartoszek; Louis C. Hirdler, both of Lake Charles, La.

[73] Assignee: Olin Corporation, New Haven, Conn.

[21] Appl. No.: 46,393

[22] Filed: Jun. 6, 1979

[51] Int. Cl.$^2$ .......................................... C07D 251/32
[52] U.S. Cl. .................................................... 544/192
[58] Field of Search ......................................... 544/192

[56] References Cited

U.S. PATENT DOCUMENTS

| | | | |
|---|---|---|---|
| 3,297,697 | 1/1967 | Reynolds et al. | 544/192 |
| 3,635,968 | 1/1972 | Goetz et al. | 260/248 |
| 3,886,153 | 5/1975 | Berkowitz | 544/192 |
| 3,953,443 | 4/1976 | Ohata et al. | 544/192 |
| 3,954,751 | 5/1976 | Fuchs | 260/248 |
| 3,994,892 | 11/1976 | Den Otter et al. | 544/192 |

*Primary Examiner*—John M. Ford
*Attorney, Agent, or Firm*—James B. Haglind; Donald F. Clements

[57] ABSTRACT

Concentrated slurries of cyanuric acid are produced in a process which comprises feeding urea to a hot solvent. In the hot solvent, the urea is pyrolyzed to produce a reaction mixture of cyanuric acid particles in the solvent. Agitation of the reaction mixture forms a suspension of cyanuric acid particles. At cyanuric acid concentrations of from about 20 to about 50 percent by weight, the cyanuric acid particles are settled from the suspension to produce a concentrated slurry phase and a supernatent solvent phase. The concentrated slurry phase is then separated from the solvent phase.

The process produces concentrated cyanuric acid slurries which minimize the complexity and cost of solvent recovery, reduces energy requirements for heating the reaction mixture and recovering the solvent, and maximizes heat transfer efficiency during the pyrolysis reaction.

11 Claims, 2 Drawing Figures

PROCESS FOR THE PRODUCTION OF CONCENTRATED CYANURIC ACID SLURRIES

This invention relates to the production of cyanuric acid. More particularly, this invention relates to the production of cyanuric acid from the pyrolysis of urea in a solvent.

Cyanuric acid can be produced by adding urea to a hot solvent medium. During the process, solid particles of cyanuric acid are formed in the hot solvent. As solvent losses or elaborate solvent recovery methods add significantly to the production cost, it is advantageous to produce concentrated slurries of cyanuric acid while minimizing the amount of solvent required and subsequent processing for its recovery.

Production of concentrated slurries of cyanuric acid by feeding large quantities of urea into the hot solvent however results in extensive scaling of reactor surfaces. The scaling causes losses in heat transfer efficiency and requires frequent cleaning of the reactor surfaces.

Previous descriptions of solvent processes for producing cyanuric acid are silent on methods of obtaining concentrated cyanuric acid slurries in which solvent losses or processing costs are minimized. They do, however, teach solvent recovery methods in which, for example, a second solvent is added to the cyanuric acid reaction mixture thereby complicating both the product and solvent recovery procedures.

It is an object of the present invention to provide a process for producing concentrated cyanuric acid slurries in which the amount and cost of solvent recovery is minimized.

Another object of the present invention is to provide a process for producing concentrated cyanuric acid slurries in which heat transfer losses are reduced while reactor productivity capacity is increased.

These and other objects of the invention are accomplished in a process for the production of concentrated cyanuric acid slurries which comprises:

(a) feeding urea to a hot solvent to pyrolyze the urea to produce a reaction mixture comprised of solid particles of cyanuric acid in the solvent, (b) agitating the reaction mixture at a first agitation rate during said pyrolysis to form a suspension of solid particles of cyanuric acid in the solvent, (c) settling the solid particles of cyanuric acid to form a concentrated lower slurry phase and an upper solvent phase, and (d) separating the concentrated lower slurry phase from the upper solvent phase.

FIG. 1 presents a flow diagram of the novel process of the present invention.

Figure 2:
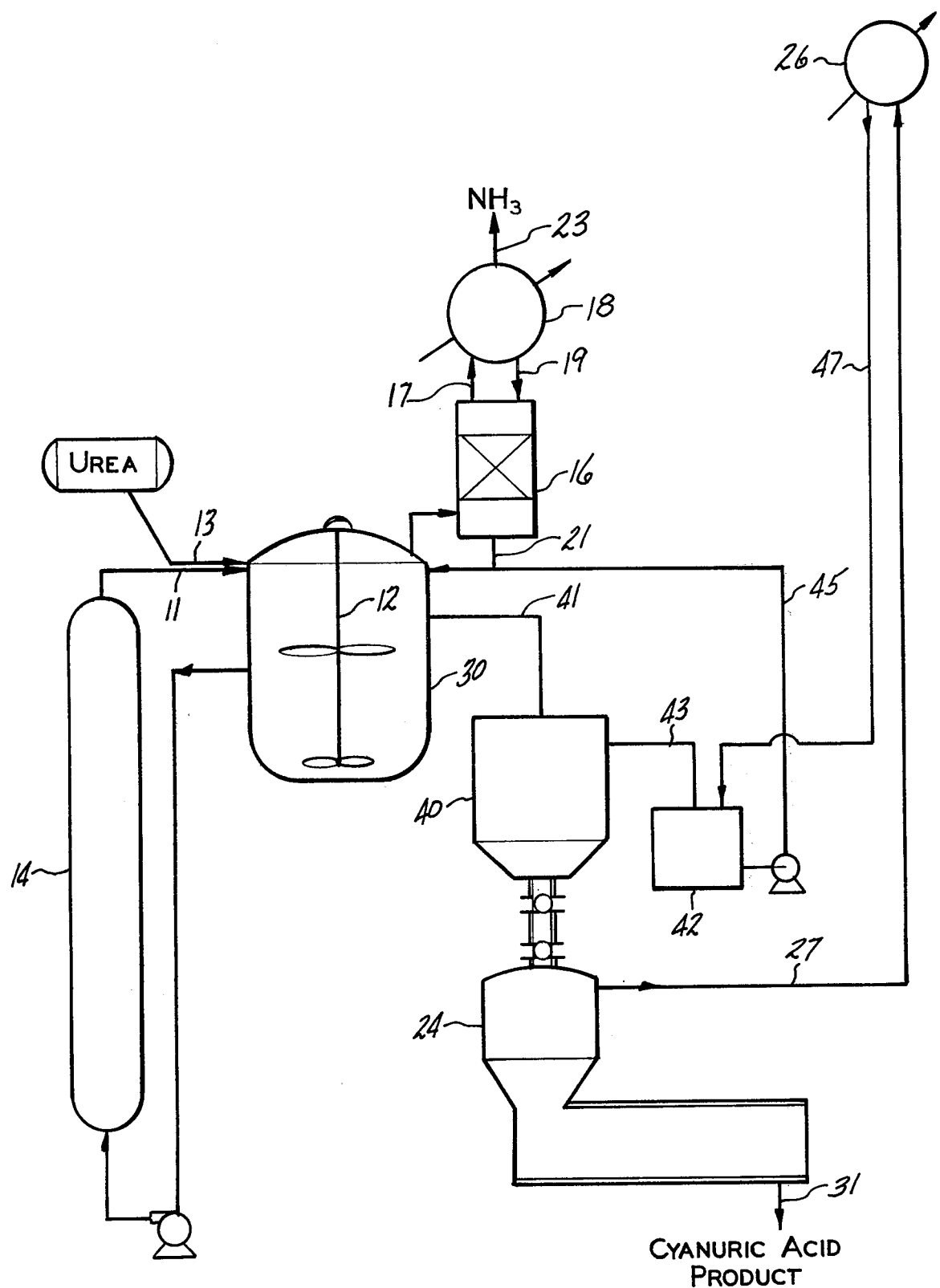

FIG. 2 illustrates an alternate embodiment of the novel process of the present invention.

FIG. 1 represents a flow diagram of the process of the present invention. Hot solvent from heat exchanger 14 is charged to reactor 10 through line 11. Molten urea is fed to reactor 10 through line 13. During the pyrolysis reaction in which cyanuric acid particles and ammonia gas are formed, agitator 12 stirs the reaction mixture to keep cyanuric acid particles in suspension. A gaseous mixture of ammonia and solvent vapors is passed from reactor 10 to scrubber 16 through line 15. The scrubbed gaseous mixture passes through line 17 to condenser 18. Condensed solvent liquid returns to scrubber 16 through line 19 and from scrubber 16 to reactor 10 through line 21. Ammonia gas is removed from condenser 18 through line 23.

Following completion of the reaction, agitator 12 is slowed or turned off and cyanuric acid particles settle to the bottom of reactor 10 as a concentrated slurry. The hot concentrated slurry is discharged through outlet 20 to flash dryer 24, the flow through line 25 being regulated by valves 22. Solvent vapors are recovered from flash dryer 24 through line 27 and fed to condenser 26. Liquid solvent is returned from condenser 26 through line 29 to scrubber 16 or alternately to heat exchanger 14. Dry cyanuric acid product is discharged from flash dryer 24 through line 31.

In an alternate embodiment illustrated in FIG. 2, cyanuric acid is continuously produced by feeding hot solvent through line 11 and urea through line 13 to reactor 30. Pyrolysis of the urea in the hot solvent produces cyanuric acid particles and ammonia gas in a reactor mixture. Agitator 12 stirs the reaction mixture to form a suspension of cyanuric acid particles. A portion of the cyanuric acid suspension continuously flows through line 41 into heated settling tank 40. Cyanuric acid particles settle to the bottom of tank 40 as a concentrated slurry. A solvent layer forms above the slurry and solvent is continuously charged through line 43 to surge tank 42 and is returned to reactor 10 through line 45. The concentrated slurry in settling tank 40 is charged to flash dryer 24 and dried as described above. Condensed solvent is returned to surge tank 42 through line 47.

In the pyrolysis process, urea is fed to a reactor containing a body of solvent. The solvent is maintained at temperatures sufficient to pyrolyze the urea, for example, in the range of from about 150° to about 300° C. During the pyrolysis process, the urea is converted to cyanuric acid in a reaction which is believed to be expressed by the following equation:

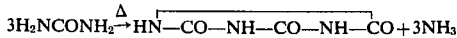

$$3H_2NCONH_2 \xrightarrow{\Delta} HN-CO-NH-CO-NH-CO + 3NH_3$$

Ammonia gas formed combines with solvent vapors to form a gaseous mixture which is removed from the reaction mixture. Solvent vapors are condensed to liquid solvent which is returned to the reactor or the solvent storage vessel. Ammonia gas is recovered by known procedures.

The solvent selected is preferably one in which the cyanuric acid has a low order of solubility. Solid particles of cyanuric acid produced are kept in suspension by agitating the reaction mixture using, for example, mechanical or gas agitation means. Agitation also contributes to the formation of suitably sized cyanuric acid crystals.

Suitable rates of agitation are employed to keep the cyanuric acid particles suspended in the solvent. For example, agitator 12 is operated at from about 100 to about 200 revolutions per minute.

Increasing concentrations of cyanuric acid in the suspension can result in loss of heat transfer efficiency and substantial deposits of cyanuric acid particles on reactor surfaces. In the process of the present invention, this is prevented by maintaining the concentration of cyanuric acid in the suspension at levels which maintain good heat transfer rates and minimize scaling of reactor surfaces. The suspensions produced have a concentration in the range of 20 to about 50 and preferably from about 25 to about 40 percent by weight of cyanuric acid.

When the suspensions have reached these concentration levels, agitation is stopped or reduced to permit the solid particles of cyanuric acid to settle to form a concentrated slurry phase at the bottom of the reactor. The cyanuric acid crystals settle rapidly, for example, at a rate of from about 0.5 to about 50 feet and preferably from about 5 to about 30 feet per minute. During the settling period a low rate of agitation is preferably employed to prevent cyanuric acid crystals from packing against the reactor bottom and inhibiting or preventing removal of the slurry from the reactor. This rate of agitation is from about 1 to about 20 revolutions per minute. The concentrated slurry phase at the bottom of the reactor contains from about 40 to about 70 and preferably from about 50 to about 65 percent by weight of cyanuric acid. Solvent content of the concentrated slurry phase is in the range of from about 30 to about 60 and preferably from about 35 to about 50 percent by weight.

The upper solvent phase which is retained in the reactor contains from about 30 to about 60 and preferably from about 35 to about 50 percent of the total amount of solvent charged to the reactor.

Separation of the concentrated cyanuric acid slurry from the solvent phase may be accomplished in several ways. In a preferred embodiment, the concentrated slurry is removed by gravity flow or pumping means from the bottom of the reaction vessel. The hot solvent phase is retained in the reactor and both solvent and heat loss is minimized.

Level control means may be employed to prevent the removal of undesired amounts of hot solvent along with the slurry. These control means monitor, for example, the percent of suspended solids in the slurry phase and in the solvent phase and, by operating valve means, stop the flow or pumping of the slurry when the solvent phase-slurry phase interface is reached. For concentrated cyanuric acid slurries in the range of from about 40 to about 70 percent by weight of cyanuric acid, a nuclear control system is preferred. In a nuclear control system, particles are emitted from a radioactive element, for example, cesium, cobalt, or radium through the slurry (and liquid) phase to a detector which is similar to a Geiger counter. Detection of the radioactive particles is inhibited by solid particles of cyanuric acid in the slurry phase. Removal of the slurry from the reactor permits increased particle detection to a predetermined level at which valve means are activated and slurry removal is stopped.

In another embodiment, the hot solvent is removed, for example, by decanting, from the reactor and introduced into a heated storage vessel or another reactor.

The hot concentrated slurry which has been separated from the solvent phase is further processed to recover a cyanuric acid product. For example, the concentrated slurries produced by the process of the present invention may be fed to a flash dryer as shown in FIG. 1. Sufficient heat is available, for example, in hot slurries having a cyanuric acid concentration of about 60–70 percent by weight to completely evaporate the solvent present under suitable vacuum conditions without requiring additional heat to the dryer. The evaporated solvent is recovered, for example, as shown in FIG. 1.

Where the production of cyanuric acid is continuous, the suspension of cyanuric acid is discharged continuously to, for example, a holding tank. The rapid settling rate of cyanuric acid particles from the solvent suspension permits the concentrated cyanuric acid slurry to be formed and removed quickly from the holding tank.

Any solvent may be used in the pyrolysis process including, for example, alkyl cyclohexanols, methoxy ethoxy isopropanols, tetrahydrofurfuryl alcohol, alkyl sulfones, dialkyl sulfones, dialkyl ethers of polyalkylene glycols, alkyl pyrrolidones, cycloalkyl pyrrolidones, diphenyl oxide, and alkyl oxazolidinones.

Processes for the pyrolysis of urea in these solvents are described, for example, in U.S. Pat. No. 3,008,961, issued Nov. 14, 1961, to B. H. Wojcik; U.S. Pat. No. 3,065,233, issued Nov. 20, 1962, to T. R. Hopkins et al; U.S. Pat. No. 3,117,968, issued Jan. 14, 1964, to K. Merkel et al; U.S. Pat. No. 3,164,591, issued Jan. 5, 1965, to W. E. Walles et al; U.S. Pat. No. 3,563,987, issued Feb. 16, 1971, to S. Berkowitz; U.S. Pat. No. 3,635,968, issued Jan. 18, 1962, to H. Goelz et al; U.S. Pat. No. 3,810,891, issued May 14, 1974, to J. M. Lee as well as Canadian Pat. No. 687,279, issued May 26, 1964, to B. H. Wojcik; Canadian Pat. No. 729,190, issued Mar. 1, 1966, to R. M. Thomas; and Canadian Pat. No. 740,444, issued Aug. 9, 1966, to R. E. Bailey et al.

The process of the present invention is able to substantially reduce:
 (1) the amount of solvent inventory required in the production of cyanuric acid,
 (2) the complexity and cost of solvent recovery,
 (3) the energy requirements for heating and recovering the solvent, and
 (4) the size of reaction vessels for producing cyanuric acid.

The novel process of the present invention is further illustrated by the following examples.

EXAMPLE 1

Molten urea was fed to a jacketed reaction vessel containing N-cyclohexyl pyrrolidone as the solvent and pyrolyzed to produce a reaction mixture containing cyanuric acid crystals. The reaction mixture was maintained at a temperature of about 200° C. and was agitated at a rate sufficient to keep the cyanuric acid particles in suspension. When sufficient urea had been pyrolyzed to form a suspension containing about 40 percent by weight of cyanuric acid, a portion of the suspension was charged to a conical bottom settling tank. The suspension was allowed to settle to form a concentrated slurry of cyanuric acid at the bottom of the reactor having a supernatant solvent layer. The concentrated slurry was discharged from the bottom of the reactor through manipulation of a ball valve. A grab sample of the solids discharging was analyzed and found to contain 56 percent by weight of cyanuric acid and 44 percent by weight of solvent. The concentrated slurry was charged to a dryer in which the remaining solvent was evaporated and the vapor fed to a condenser for recovery. A cyanuric acid product was recovered from the dryer containing about 0.1 percent by weight of solvent.

This example illustrates the production of a solvent-free product using the process of the present invention.

EXAMPLE 2

Urea was pyrolyzed in N-cyclohexylpyrrolidone solvent using the procedure of Example 1. Following completion of the reaction, the hot suspension was allowed to settle to form a concentrated slurry of cyanuric acid at the bottom of the reactor with a supernatant solvent layer. Cyanuric acid particles settled from the suspension at a rate of about 10 feet per minute. Following settling, the hot solvent layer was removed from the reactor by decanting and pumped to a heated storage vessel. The concentrated slurry containing about 55 percent by weight of cyanuric acid and 45 percent by weight of solvent was removed from the bottom of the reactor by gravity flow. The decanted hot solvent (65 percent of the total solvent charged) was pumped back into the reactor for use in additional cyanuric acid production.

This example shows an embodiment of the process of the present invention in which a major portion of the solvent employed is readily separated from the cyanuric acid slurry which is to be further processed. Solvent recovery procedures and energy requirements are substantially reduced.

EXAMPLE 3

Molten urea is fed to a jacketed reaction vessel containing N-cyclohexyl pyrrolidone as the solvent. The reaction vessel is equipped with a variable speed, dual impeller agitator. During the pyrolysis reaction, the agitator runs at 150 rpms to provide the necessary mixing action to insure complete reaction and good heat transfer. At the end of the pyrolysis reaction when the solid cyanuric acid concentration is 40 percent by weight, the agitator speed is reduced to 5 rpms to allow cyanuric acid crystals to settle and form a hot concentrated slurry phase containing 57 percent by weight of cyanuric acid. After about 5 minutes has passed to allow settling of the crystals, the bottom outlet valve is opened to allow the concentrated slurry to discharge by gravity to the next processing vessel. A nuclear level detection device is used to determine when the concentrated cyanuric acid slurry transfer is complete. After discharge of the concentrated slurry, the bottom outlet valve is closed and the hot solvent phase containing 50 percent of the total solvent used is retained in the reaction vessel.

This example illustrates the production of a concentrated cyanuric acid slurry where solvent handling is minimized and energy costs reduced.

What is claimed is:

1. A process for the production of concentrated cyanuric acid slurries which comprises:
   (a) feeding urea to a hot solvent to pyrolyze said urea to produce a reaction mixture comprised of solid particles of cyanuric acid in said solvent,
   (b) agitating said reaction mixture at a first agitation rate during said pyrolysis to form a suspension of said solid particles of cyanuric acid in said solvent,
   (c) reducing said first agitation rate to permit settling of said solid cyanuric acid particles from said suspension to form a concentrated lower slurry phase and an upper solvent phase, where said concentrated lower slurry phase comprises from about 40 to about 70 percent by weight of cyanuric acid, and
   (d) separating said concentrated lower slurry phase from said upper solvent phase.

2. The process of claim 1 in which said suspension comprises from about 20 to about 50 percent by weight of said solid particles of cyanuric acid.

3. The process of claim 2 in which said first agitation rate is from about 100 to about 200 rpms.

4. The process of claim 1 in which a second agitation rate of from about 1 to about 20 rpms is employed during the settling of said solid cyanuric acid particles.

5. The process of claim 1 in which said separation of said concentrated lower slurry phase from said upper solvent phase is accomplished by gravity flow of said concentrated lower slurry phase.

6. The process of claim 1 in which separation of said concentrated lower slurry phase from said upper solvent phase is accomplished by decanting said upper solvent phase.

7. The process of claim 5 or 6 in which an interface between said upper solvent phase and said concentrated lower slurry phase is detected by a level control means.

8. A continuous process for the production of cyanuric acid which comprises:
   (a) feeding simultaneously urea and a hot solvent to a reaction zone to produce a reaction mixture comprised of solid particles of cyanuric acid in the solvent, said reaction mixture comprising from about 25 to about 40 percent by weight of cyanuric acid,
   (b) agitating said reaction mixture to form a suspension of solid particles of cyanuric acid in said solvent,
   (c) continuously removing a portion of said suspension from said reaction zone to a separating zone,
   (d) settling said solid particles of cyanuric acid from said suspension to form a concentrated lower slurry phase and an upper solvent phase, said concentrated lower slurry phase containing from about 50 to about 65 percent by weight of cyanuric acid, and
   (e) separating said concentrated lower slurry from said upper solvent phase.

9. The process of claim 8 in which a portion of said upper solvent phase is continuously introduced into a solvent recovery zone.

10. The process of claim 9 in which said concentrated lower slurry phase is separated from said upper solvent phase by gravity flow of said concentrated lower slurry phase.

11. The process of claim 8 or 10 in which an interface between said upper solvent phase and said concentrated lower slurry phase is detected by a level control means.

* * * * *